United States Patent
Haddock et al.

(10) Patent No.: US 7,879,009 B1
(45) Date of Patent: Feb. 1, 2011

(54) VARIABLE OPENING DELIVERY SYSTEM FOR INTERVERTEBRAL DISC THERAPIES

(75) Inventors: Sean M. Haddock, Memphis, TN (US); Susan J. Drapeau, Cordova, TN (US); Thomas Andrew Simonton, Memphis, TN (US)

(73) Assignee: Warsaw Orthopedic, Inc.

( * ) Notice: Subject to any disclaimer, the term of this patent is extended or adjusted under 35 U.S.C. 154(b) by 0 days.

(21) Appl. No.: 12/696,153

(22) Filed: Jan. 29, 2010

(51) Int. Cl.
*A61M 5/178* (2006.01)
*A61M 29/00* (2006.01)
*A61B 1/32* (2006.01)

(52) U.S. Cl. .................. 604/164.03; 604/22; 604/104; 604/164.06; 600/219; 600/210; 606/108; 606/71; 606/198

(58) Field of Classification Search .......... 604/21–22, 604/96.01, 103.14, 104–109, 115–117, 148, 604/161–162, 164.01, 164.03, 164.04, 164.06–164.12, 604/166.01, 170.01–170.03, 171, 177, 264, 604/272; 606/1, 29, 45, 52, 167, 170, 108, 606/71, 198; 600/564–567, 219, 210
See application file for complete search history.

(56) References Cited

U.S. PATENT DOCUMENTS

| | | | |
|---|---|---|---|
| 3,788,318 A * | 1/1974 | Kim et al. .............. 604/164.03 |
| 4,431,426 A * | 2/1984 | Groshong et al. ........... 604/523 |
| 5,030,201 A | 7/1991 | Paestrant |
| 5,092,848 A * | 3/1992 | deCiutiis ............... 604/170.01 |
| 5,152,396 A * | 10/1992 | Chen et al. .................... 206/49 |
| 5,195,507 A * | 3/1993 | Bilweis ......................... 600/204 |
| 5,236,424 A * | 8/1993 | Imran ......................... 604/523 |
| 5,309,641 A * | 5/1994 | Wonderley et al. ............. 30/339 |
| 5,357,974 A * | 10/1994 | Baldridge .................. 600/567 |
| 5,431,671 A * | 7/1995 | Nallakrishnan ............. 606/167 |
| 5,431,672 A * | 7/1995 | Cote et al. ................... 606/167 |
| 5,707,359 A * | 1/1998 | Bufalini ....................... 604/104 |
| 5,843,017 A * | 12/1998 | Yoon ............................ 604/22 |
| 5,938,635 A * | 8/1999 | Kuhle .......................... 604/506 |
| 5,971,960 A * | 10/1999 | Flom et al. ................... 604/174 |
| 6,162,203 A * | 12/2000 | Haaga .......................... 604/272 |
| 6,197,002 B1 * | 3/2001 | Peterson ................. 604/164.01 |
| 6,248,128 B1 | 6/2001 | Berry et al. |
| 6,336,937 B1 | 1/2002 | Vonesh et al. |
| 6,863,674 B2 * | 3/2005 | Kasahara et al. ............ 606/108 |
| 7,179,225 B2 * | 2/2007 | Shluzas et al. .............. 600/219 |
| 7,585,290 B2 * | 9/2009 | Kathrani et al. ............. 604/264 |
| 7,594,888 B2 * | 9/2009 | Raymond et al. ........... 600/219 |
| 7,628,802 B2 | 12/2009 | White et al. |
| 2003/0130654 A1 * | 7/2003 | Kasahara et al. .............. 606/45 |
| 2003/0191371 A1 * | 10/2003 | Smith et al. .................. 600/210 |
| 2004/0097907 A1 * | 5/2004 | DiPoto .......................... 606/1 |
| 2004/0098012 A1 * | 5/2004 | Davison et al. ............. 606/190 |
| 2005/0075548 A1 * | 4/2005 | Al-Ali et al. ................. 600/322 |

(Continued)

OTHER PUBLICATIONS

Charles L. Branch, M.D., Arthur H. Conley, M.D., MAST QUADRANT, Retractor System, medial lateral Blades Procedures Solutions Technique, Medtronic Spinal and Biologics Business, Memphis, Tennessee.

*Primary Examiner*—Nicholas D Lucchesi
*Assistant Examiner*—Quynh-Nhu H Vu

(57) ABSTRACT

The disclosure is directed to a needle system configured to enlarge an access path in a patient without further cutting into the tissue of the patient so as to reduce recovery time and trauma to the patient. Also provided are methods of using the needle system provided.

9 Claims, 8 Drawing Sheets

U.S. PATENT DOCUMENTS

2005/0159711 A1* 7/2005 Kathrani et al. ............. 604/264
2006/0106416 A1* 5/2006 Raymond et al. ........... 606/198
2007/0010843 A1* 1/2007 Green ........................ 606/185
2007/0270655 A1* 11/2007 Smith et al. .................. 600/210
2008/0103441 A1* 5/2008 Melsheimer ............. 604/96.01

* cited by examiner

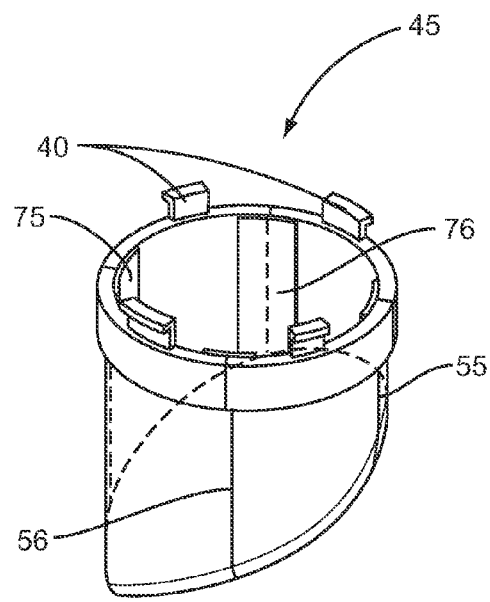
FIG. 1C
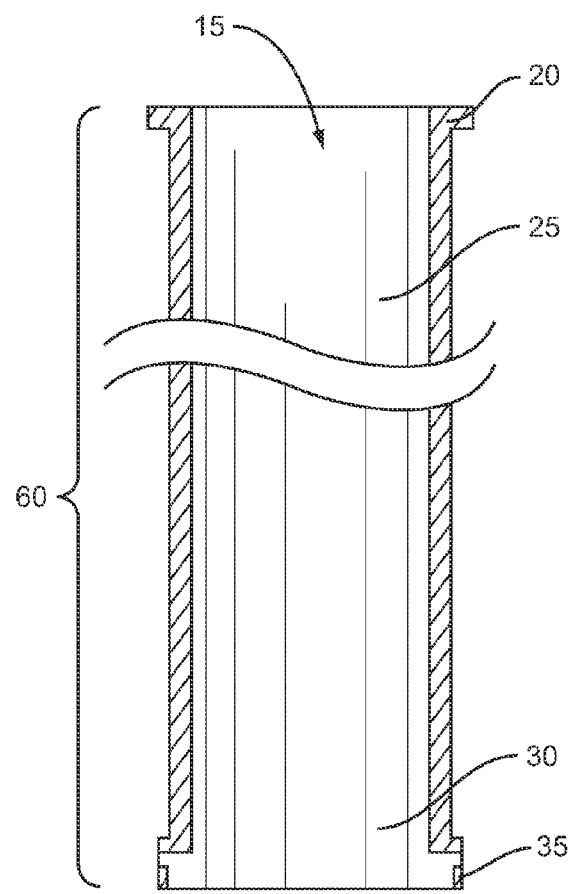
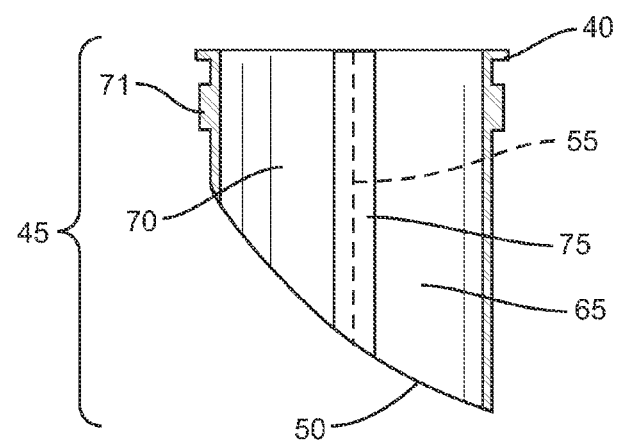
FIG. 2

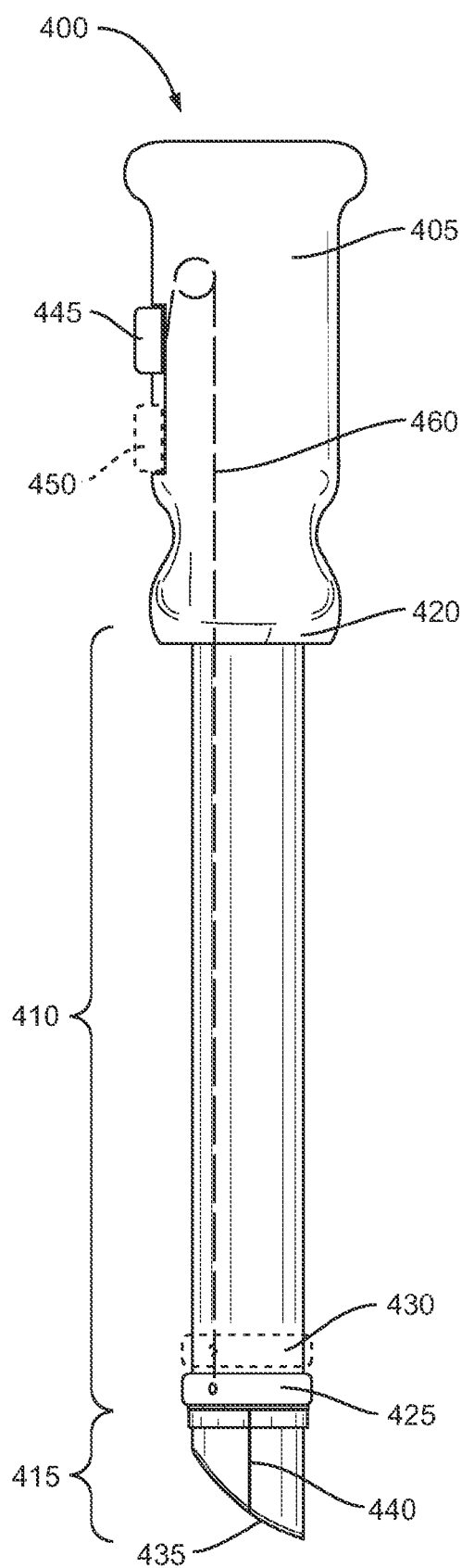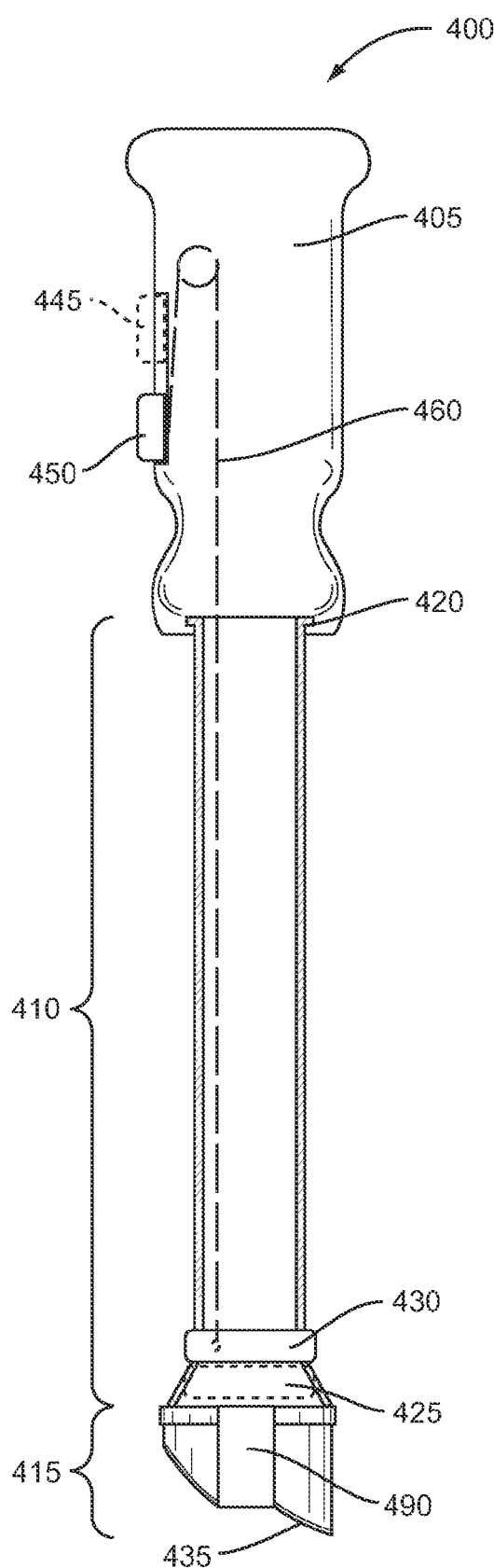
FIG. 3A                    FIG. 3B

_US 7,879,009 B1_

VARIABLE OPENING DELIVERY SYSTEM FOR INTERVERTEBRAL DISC THERAPIES

TECHNICAL FIELD

The present disclosure generally relates to a variable opening delivery system that can be used for intervertebral disc therapies as well as other procedures. In particular, the present disclosure relates to an orthopedic needle assembly system effective to expand the access opening in a patient without further cutting into the surface of the patient.

BACKGROUND

Needles may be used to transfer an agent, drug or other substance into a patient. In addition needles can be used to extract tissue/fluids from a patient for biopsy or other therapeutic analysis. The needle may be inserted into the patient at a desired location. The needle may be hollow and include a hollow tip. A syringe with a drug may be attached to an end of the needle so that the drug may flow from the syringe, through the hollow needle, through the needle tip and into the patient. As stated above, the needle may also be used to extract tissue/fluid from an area where the needle is placed.

Some therapies require large extraction of tissue/fluid from the patient or a delivery of large quantities of therapeutic agents to a location and therefore may require the use of large needle/instrument to achieve this task. However, using a large needle/instrument requires a large access path in a patient, such as an incision, that leads to more tissue disruption than if a smaller access path is used. The present disclosure describes an improvement over these prior art technologies.

SUMMARY OF THE INVENTION

Accordingly, one embodiment of the present invention is directed to an orthopedic needle assembly comprising a needle comprising a hollow shaft having opposed distal and proximal ends and a lumen extending from the distal end of the hollow shaft and terminating at an opening on the proximal end of the hollow shaft. The distal end having an expandable needle head having a cutting surface configured for penetration into an intervertebral disc of a patient. The cutting surface having a sharpened edge extending along at least a portion of a bottom of the expandable needle head.

Another embodiment of the present invention is directed to an orthopedic needle assembly kit comprising a needle and a plurality of expandable needle heads. The needle comprising a hollow shaft having opposed distal and proximal ends and a lumen extending from the distal end of the hollow shaft and terminating at an opening on the proximal end of the hollow shaft. The distal end configured to accept an expandable needle head. The kit further comprising a plurality of differently configured expandable needle heads. Each of the needle heads are configured to removably attach to the distal end of the hollow shaft and have a cutting surface configured for penetration into a surface of a patient such as the intervertebral disc of the patient. The cutting surface having a sharpened edge extending along at least a portion of a bottom of each of the expandable needle heads and each of the expandable heads having an increasing number of expandable segments.

Another embodiment of the present invention is directed to an orthopedic needle assembly comprising a needle having a hollow shaft with opposed distal and proximal ends. The distal end having a cutting edge configured for penetration through a surface of a patient, such as of the intervertebral disc, in order to cut into the surface and provide a small access path into the patient. The hollow shaft having a lumen extending from the proximal end of the hollow shaft and terminating at an opening at the distal end of the hollow shaft. The needle assembly also has at least one dilator tube having a lumen larger than the hollow shaft of the needle. The dilator tube is configured to fit over the hollow shaft of the needle so that it can be wedged into the access hole cut in the patient, such as an access hole cut into the surface of a intervertebral disc causing the perimeter of the cut surface of the intervertebral disc to enlarge without further cutting the surface of the intervertebral disc. The dilator tubes are configured to have blunt edges so as not to make additional cuts at the access hole or with the patient.

Yet another embodiment of the present invention is directed to an orthopedic needle assembly kit comprising a needle having a hollow shaft having opposed distal and proximal ends. The distal end having a cutting edge configured for penetration into the surface of a patient such as the surface of the intervertebral disc. The hollow shaft having a lumen extending from the proximal end of the hollow shaft and terminating at an opening of the distal end of the hollow shaft. Also included in the needle assembly kit is a plurality of dilator tubes having increasing larger diameters and blunt ends. The needle assembly kit further comprising a case configured to hold the needle and the plurality of dilator tubes.

Additional embodiments of the present invention are directed to methods designed to utilize the orthopedic needle assemblies of the present disclosure. Additional features and uses of the present invention are further described in connection with the figures in the detailed description section below.

BRIEF DESCRIPTION OF THE DRAWINGS

The present disclosure will become more readily apparent from the specific description accompanied by the following drawings, in which:

FIG. 1c is a cut-away view of the connecting portion needle head;

FIG. 2 is a side cut-away view of one particular embodiment of the needle assembly of the present invention showing the needle attached to the expandable needle head in accordance with the principles of the present disclosure;

FIG. 3A is a side cut-away view of one particular embodiment of the needle assembly of the present invention showing the needle attached to the expandable needle head and manipulator handle in accordance with the principles of the present disclosure;

FIG. 3B is a side cut-away view of one particular embodiment of the needle assembly of the present invention showing the needle attached to the expandable needle head wherein the head is in the expanded view and a manipulator handle in accordance with the principles of the present disclosure;

Like reference numerals indicate similar parts throughout the figures.

DETAILED DESCRIPTION OF THE INVENTION

Figures 1A, 1B:
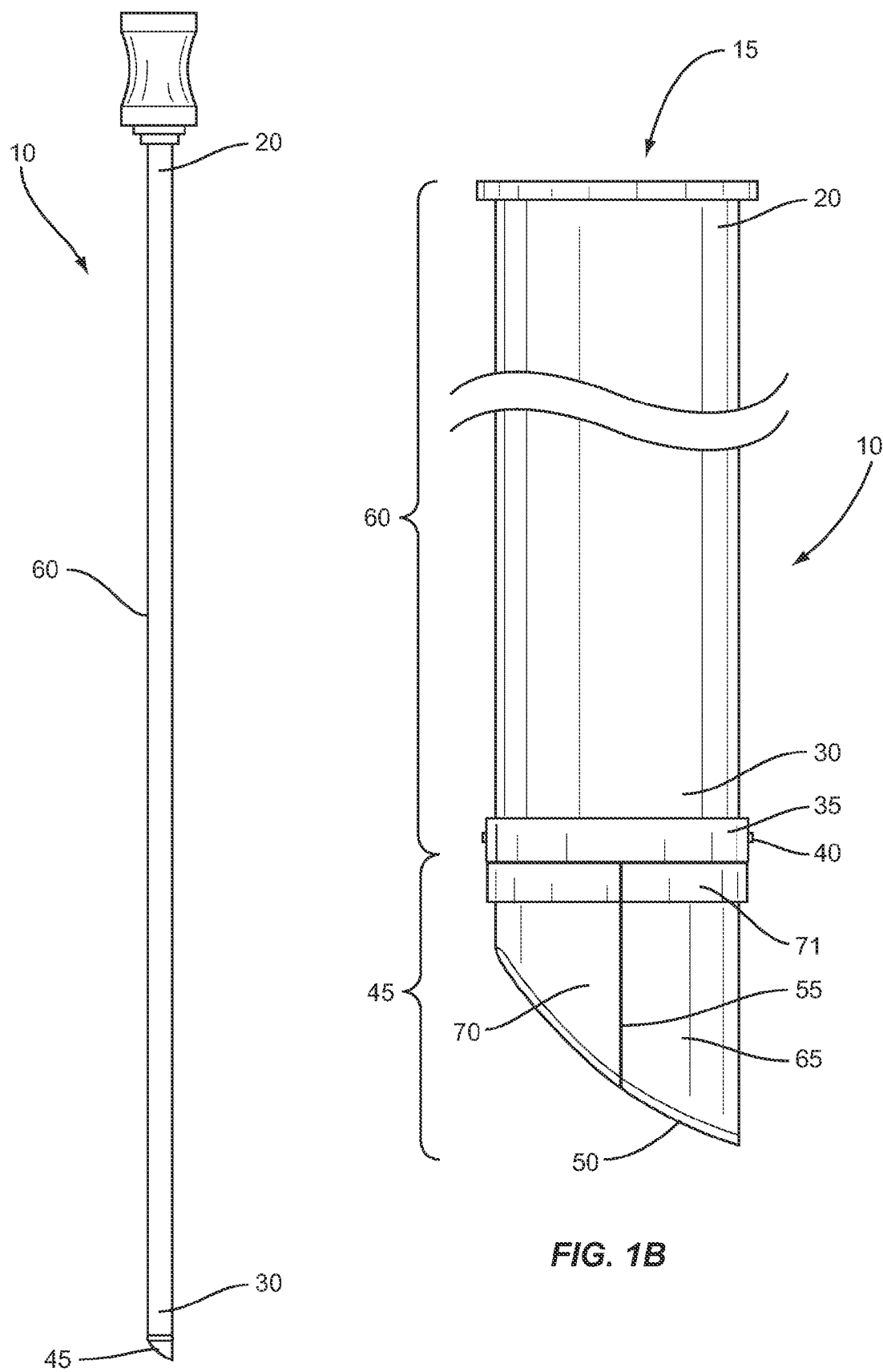
FIG. 1a is a side view of one particular embodiment of the needle assembly of the present invention showing the needle detached from the expandable needle head in accordance with the principles of the present disclosure.
FIG. 1b is a side view of one particular embodiment of the needle assembly of the present invention showing the needle detached from the expandable needle head in accordance with the principles of the present disclosure.

The exemplary embodiments of the needle assembly and methods of use disclosed are discussed in terms of medical treatment devices and more particularly, in terms of a needle assembly and method for treating the orthopedic conditions.

It is envisioned that the needle assembly system and methods of use of the present invention provide improved access into a patient for delivery of a therapeutic agent and/or extraction of tissue/fluid using a needle inserted in a patient. It is further envisioned that the present invention may be employed to provide a larger access path than using convention needle systems with minimal tissue damage.

It is contemplated that the present invention may be employed with surgical treatments, percutaneous and minimally invasive procedures of such disorders, such as, for example, arthroplasty to maintain motion, arthrodesis including fusion, bone graft and implantable prosthetics, tissue biopsy including those associated with diagnostics and therapeutics.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a needle system, related components and exemplary methods of employing the needle assembly of the present invention in accordance with the principles of the present disclosure. Alternate embodiments are also disclosed. Reference will now be made in detail to the exemplary embodiments of the present disclosure, which are illustrated in the accompanying figures. Turning now to FIGS. 1-8, there are illustrated components of the needle guide system in accordance with the principles of the present disclosure.

The components of the orthopedic needle assembly system are fabricated from materials suitable for medical applications, including metals, synthetic polymers, ceramics, biocompatible materials and/or their composites, including but not limited to Gore-Tex®, polyethylene, nylon, balloon materials, and the like, depending on the particular application and/or preference of a medical practitioner. For example, components of the orthopedic needle assembly discussed below, may be monolithically formed, integrally connected or configured as an insert, can be coated with materials that reduce friction or tearing of tissue in which the needle is inserted. Different components of the orthopedic needle assembly may have alternative material composites to achieve various desired characteristics such as strength, rigidity, elasticity, compliance, biomechanical performance, durability and radiolucency or imaging preference. The components of the orthopedic needle assembly may also be fabricated from a heterogeneous material such as a combination of two or more of the above-described materials.

Referring to FIGS. 1a, 1b and 1c an orthopedic needle assembly system 10 in accordance with the disclosure includes a needle 60, at least one expandable needle head 45 that is configured to attach to the needle 60. The needle 60 having a proximal end 20 and a distal end 30. The proximal end 20 having an opening 15 that is continuous with a lumen 25 that extends from the proximal end 20 of the needle 60 to the distal end 30 of the needle 60. At the distal end 30 of needle 60 is an attaching joint 35 configured to interact with an attaching joint 40 on the expandable needle head 45. This configuration allows for the connection of the expandable needle head 45 to the distal end 30 of the needle 60 to form a complete needle assembly 10. Once attached, the lumen 25 of the needle 60 becomes continuous with the lumen of the expandable needle head 45.

The expandable needle head 45 is configured to have a cutting surface. The cutting surface is configured to have a sharpened cutting edge 50 along at least a portion of the bottom of the cutting surface of the expandable needle head 45. The cutting edge 50 is sharp enough to penetrate into a surface of a patient, such as the surface of an intervertebral disc. The cutting edge 50, as well as the rest of the expandable needle head 45, may be coated with a biological compatible lubricate and/or coating designed to reduce tissue damage at the cutting edge 50 as it cuts into the surface. The cutting edge can also be configured or coated with a coating that causes cauterization of the incision when being made.

In one embodiment of the present invention, the expandable needle head 45 is configured to have a plurality of segments (65 and 70—shown in FIG. 2) and a slidable retention band 71. The slidable retention band 71 is configured to at least partially overlap the plurality of segments (65 and 70) at the upper region of the expandable needle head 45. The number of segments in the expandable head can vary from 2 to about 6 and are configured to have ductile hinges (75,76,80 and 81) interconnecting each of the segments (see FIGS. 4a-4h which are described below). The ductile hinges allow the expansion of the expandable head 45 from an initial diameter to a larger diameter. That is, segments (65 and 70) and ductile hinges (75 and 76 shown in FIG. 4a-h) are interconnected in an alternating arrangement to form a substantially cylindrical tube having a lumen that is continuous with the lumen 25 of needle 60 but is larger in diameter than the initial diameter of the expandable head 45.

The substantially cylindrical tube shown in FIGS. 4a-h is configured to expand or compress from a first diameter to a second diameter by deformation of the ductile hinges without substantial deformation of the segments attached to the ductile hinges. In other words, the plurality of ductile hinges connecting two adjacent segments is configured to deform resiliently upon radial expansion or compression of the expandable needle head 45.

The retention band 71 is configured so that it can move from a first position to a second position. The retention band 71 is designed so as to retain the expandable needle head 45 in the compressed configuration when in a first position and as the retention band 71 moves to the second position the expandable needle head 45 expands to have a larger diameter. That is, when the retention band 71 moves to a second position either as the needle head is advanced into the patient or by a mechanical advancement, the expandable needle head 45 expands separating the segments. Once the segments separate the ductile hinges slide into the void created by the separation of the parting segments 70 and 65 to form a substantially cylindrical tube having a lumen that is continuous with the lumen of the needle 60. The retention band 71 can be spring loaded to advance from a first position to a second position as the expandable needle head 45 is advanced into a patient.

In an alternative embodiment the retention band 71 is attached to an actuator that when actuated causes movement of the retention band 71 and expansion of the expandable head 45. The actuator can be activated to move back to the first position so that the segments of the expandable needle head 45 are compressed and the ductile hinges and segments return to their original position so that the diameter of the expandable head 45 is small enough to be removed from the original access hole without further tissue damage.

This configuration allows the expandable needle head 45 to expand to a larger diameter once the needle head is either at or below the surface of the patient in which it is being inserted. The larger diameter can be beneficial for procedures that require a larger needle but with the present invention the access path remains small. For example, if the needle assembly is being used for extracting tissue and/or fluid form a patient; a larger diameter would allow tissue/fluid to be taken from a larger area. Using the present invention this can be achieved without further increasing the size of the access hole produced by the needle. This allows a surgeon to make a small access hole in the patient while having greater access to the tissue below the surface once the expandable head is expanded. As stated above, the smaller the access hole, the less recovery time for the patient.

It is understood that the needle 60 may be detachably connected to expandable needle head 45 by friction fit, screw and thread, tongue and groove, protuberance and/or hole arrangements. In addition, a syringe may also be attached to the proximal end 20 of the needle 60 using a friction fit, screw and thread, tongue and groove, protuberance and/or hole arrangements.

In the embodiment shown in FIG. 1 the needle is shown having at least one wall defining a substantially hollow cylinder with an internal lumen 25. The expandable needle head 45 is shown in FIG. 1 to have a cutting edge with a diagonal slant. The slanted cutting edge facilitates entry of the point located at the lower end of the slant to puncture the skin first so that an access hole can be created as the needle is advance into the patient. In the alternative, the cutting edge can be flat so that the full diameter of the expandable cutting edge is used to create the access hole. Other configurations known in the art for the cutting edge can also be used with the present invention. As stated above, it is also contemplated that the cutting surface can be coated with therapeutic agents and/or pharmacological agents, such as analgesics, anesthetics, and/or growth factors.

Referring also to FIG. 2, the needle assembly 10 is shown with the needle 60 attached to the expandable needle head 45. In this configuration the distal end 30 of the needle 60 is attached to the expandable needle head 45 by overlapping of the attaching joint of the needle 35 and the attaching joint of the expandable needle head 40. This connection can be achieved by a friction or interference engagement to fix the position of needle 60 relative to the expandable needle head 45. In the alternative, the needle 60 can be attached to the expandable needle head 45 using a screw and thread, tongue and groove, protuberance and/or hole arrangement so as to fix the needle 60 to the expandable needle head 45.

Referring to FIG. 3A, the needle assembly 400 is shown having a manipulator handle attached to the needle 420. This attachment can be achieved by a friction or interference engagement, screw and thread, tongue and groove, protuberance and/or hole arrangement so as to attach the manipulator handle 405 to the needle 410. The manipulator handle 405 can be equipped with a trigger having a first trigger position 445 that can be advanced to a second trigger position 450. Although FIG. 3A shows a particular configuration for the manipulator handle, other configuration can be used that achieve the same objective and therefore fall within the scope of the invention.

The trigger of the manipulator handle is configured to be in communication with a retention band. The retention band is in the first position 425 when the trigger is in the first position 445. In this position the expandable needle head 415 is compressed. As the trigger is moved from a first position 445 to a second position 450, the retention band moves from a first position 425 to a second position 430 and the expandable needle head is allowed to expand to a diameter larger than the initial diameter. That is, the segments separate and the ductile hinges 490 (FIG. 3b) fill the space so as to create a substantially cylindrical tube having a lumen continuous with the lumen of needle 410. In the alternative, manipulator handle 405 can be configured not to include a trigger in communication with the retention band and the retention band can be advanced form a first position 425 to a second position 430 as the needle assembly is advanced into the patient. This would cause the expandable needle head to expand and compress as the needle is advanced into the patient and removed from the patient and the retention band moves to a second position on advancement of the needle and back to the first position 425 when the needle is withdrawn from the patient. It should be understood that alternate actuating mechanisms can used to move the retention band from a first position to a second position as described above, all of which fall within the spirit of the present invention.

It is contemplated that number of segments in the expandable needle head 415 as well as the size of the opening created when expanded may be variously sized and configured according to a particular needle applications. It is further contemplated that expandable needle head 415 and/or portions thereof may be rigid, semi-rigid and/or flexible to facilitate cutting and/or expansion of the needle head.

It is also contemplated that the cross-sectional geometry of needle can have various configurations, for example, round, oval, oblong, triangular, rectangular, polygonal, irregular, uniform, non-uniform, consistent or variable. It is further contemplated that the diameter or thickness of needle walls forming the lumen shaft may be offset, tapered, converging and/or diverging.

Figure 4A:
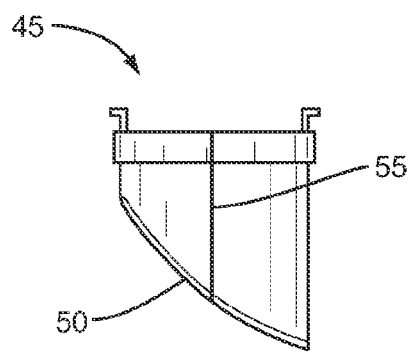
FIGS. 4A-4H showing several cut-away side and top views of the expanded and non-expanded needle heads in accordance with the principles of the present disclosure.
Figure 4B:
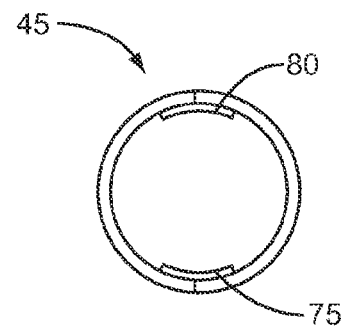
Figure 4C:
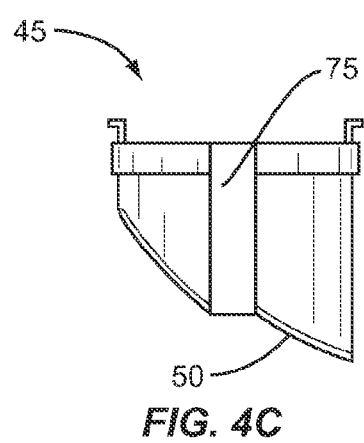
Figure 4D:
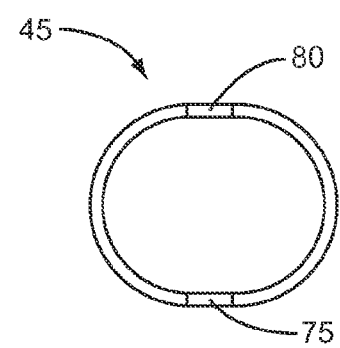
Figure 4E:
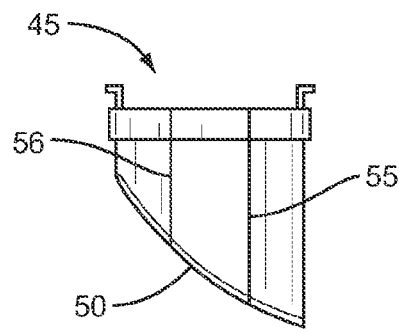
Figure 4F:
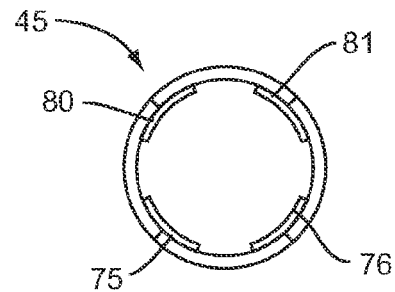

Various configurations of expandable needle head 45 are shown in FIGS. 4a-4h. FIG. 4a shows a side view of an expandable needle head 45 having two segments sharing a common line 55. FIG. 4b shows a cross-sectional top view of the expandable needle head 45 in FIG. 4a further detailing a first ductile hinge 75 positioned across a common point of the two segments and a second ductile hinge 80 positioned across a common point of the two segments. FIG. 4c shows the expandable needle head 45 in and expanded position wherein the first ductile hinge 75 fills the void created by the two segments coming apart. The diameter of the expandable needle head is greater than the diameter of the compressed needle head 45 shown in FIG. 4a. FIG. 4d shows a cross-sectional top view of the expandable needle head 45 of FIG. 4c. Similarly, FIG. 4e shows an expandable head 45 having four segments sharing two common surfaces 55 and 56. FIG. 4f shows a cross-sectional top view of the expandable needle head in FIG. 4e.

Figure 4G:
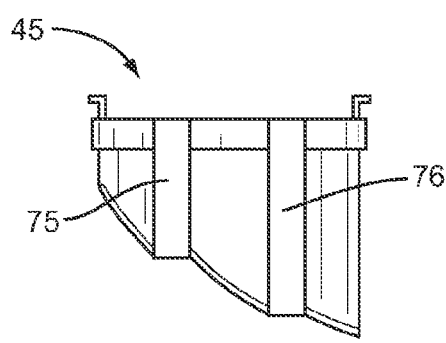
Figure 4H:
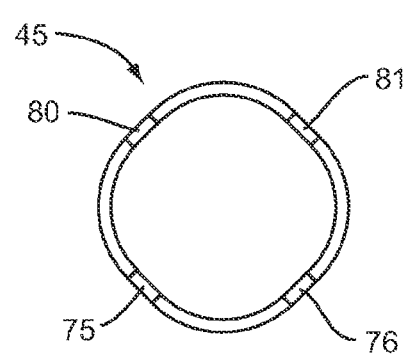

FIGS. 4g and 4h show the expandable needle head with the ductile hinges in place. As with the diameter of the expandable needle head having 2 segments, the diameter of the needle head in the expanded configuration is larger than in the compressed configuration and the substantially cylindrical tube shares a common lumen with the needle. This allows tissue/fluid to be abstracted from the patient form a larger area while keeping the access path small. Similarly, delivery of a therapeutic can be administered to a greater area when the needle is in the expanded configuration.

Figure 5:
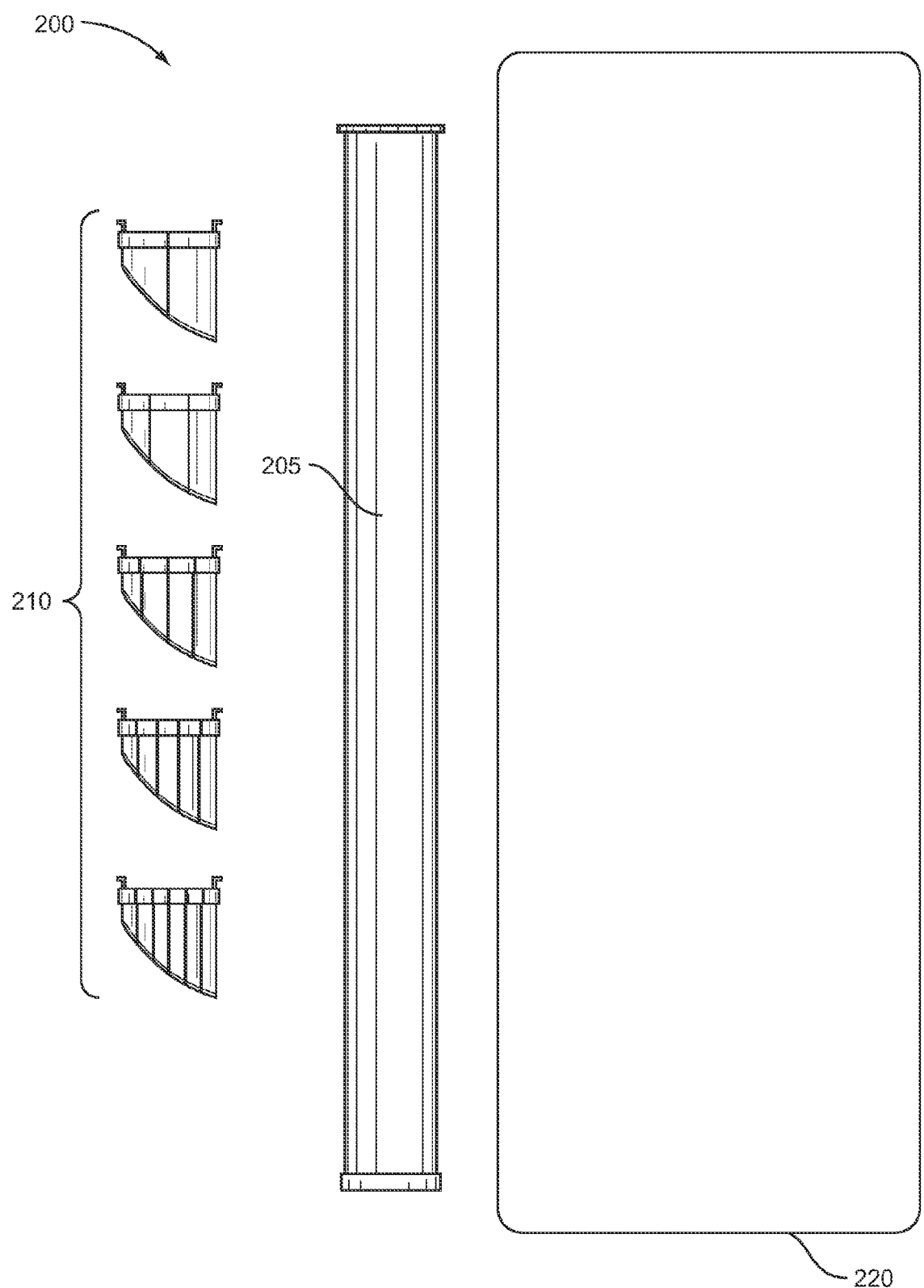
FIG. 5 is a side cut-away view of the needle assembly kit with expandable needle heads in accordance with the principles of the present disclosure.

The needle 60 of the present invention can be configured to attach expandable needle heads of different configurations. That is, needle heads having from 2 to 6 segments can be used to reach a spectrum of diameters. FIG. 5 shows a kit containing a needle 205 and a multiple of needle heads 210 each having a different number of segments. Different expandable needle heads 210 can be chosen according to the particular medical procedure being performed. The components of the kit can be contained in a case 220 that may or may not be in a pre-sterilized package from the factory. The kit can also made to be disposable or in the alternative, made from durable material such as stainless steel, ceramics, composites and the like that can be sterilized between uses.

Figure 6:
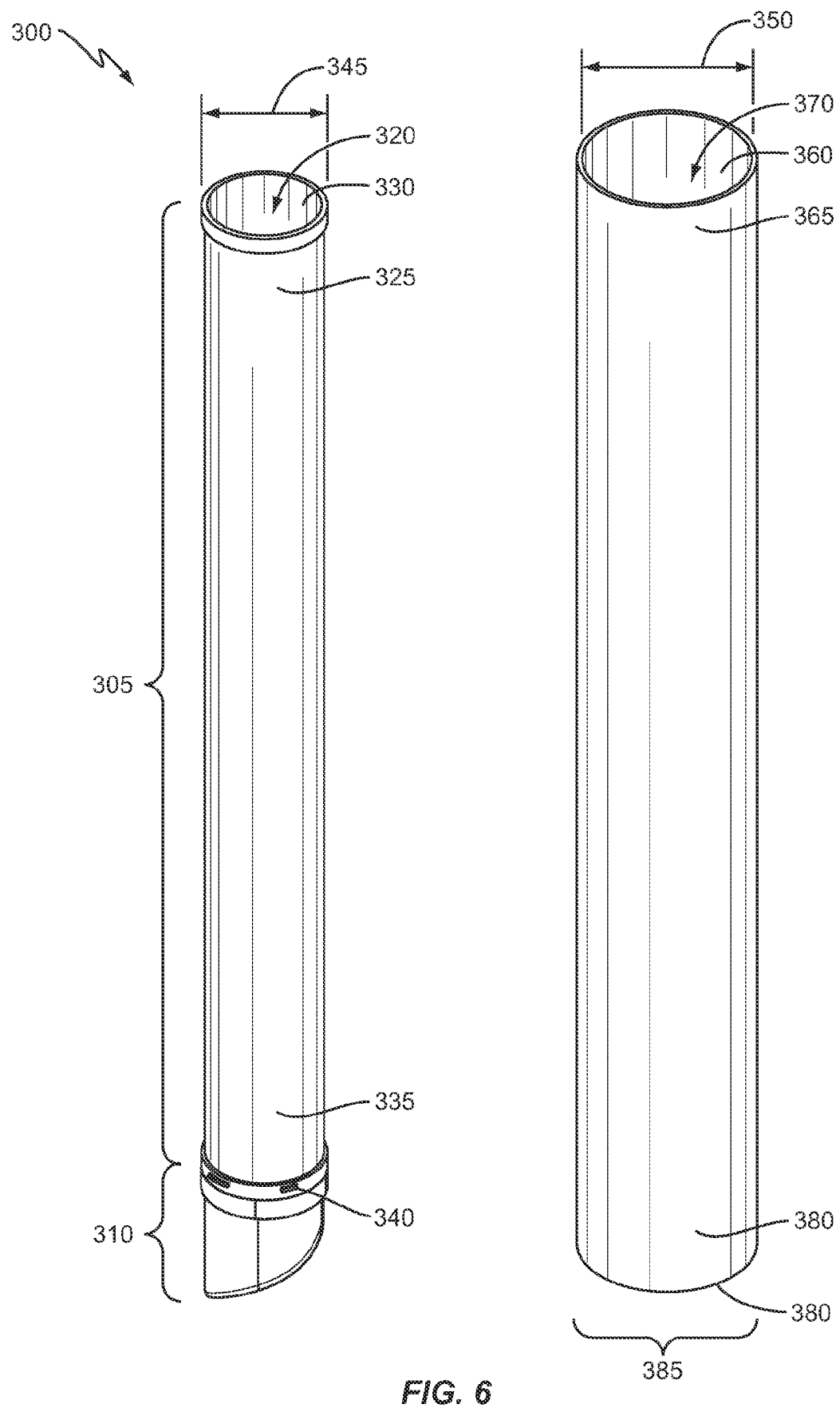
FIG. 6 is a side cut-away views of one particular embodiment of the needle assembly of the present invention showing the needle and dilator in accordance with the principles of the present disclosure.
Figure 7A:
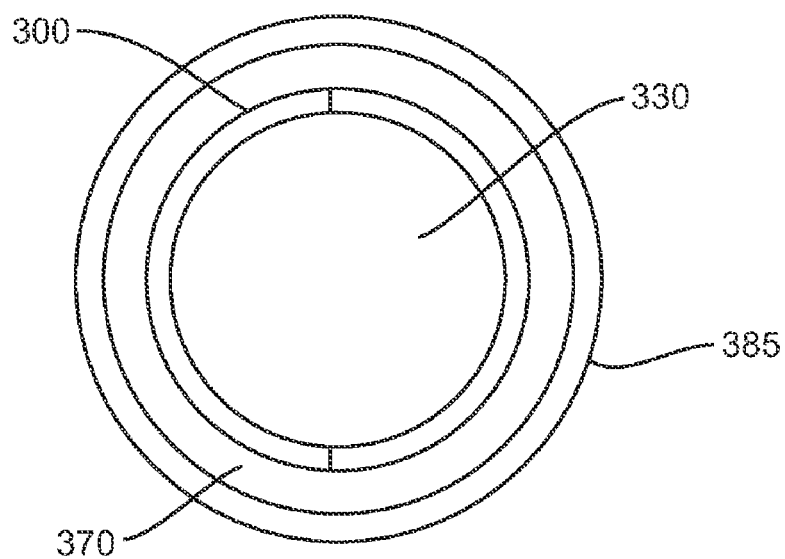
FIG. 7A is a top end view of the needle with one dilator tube positioned over the needle in accordance with the principles of the present disclosure.
Figure 7B:
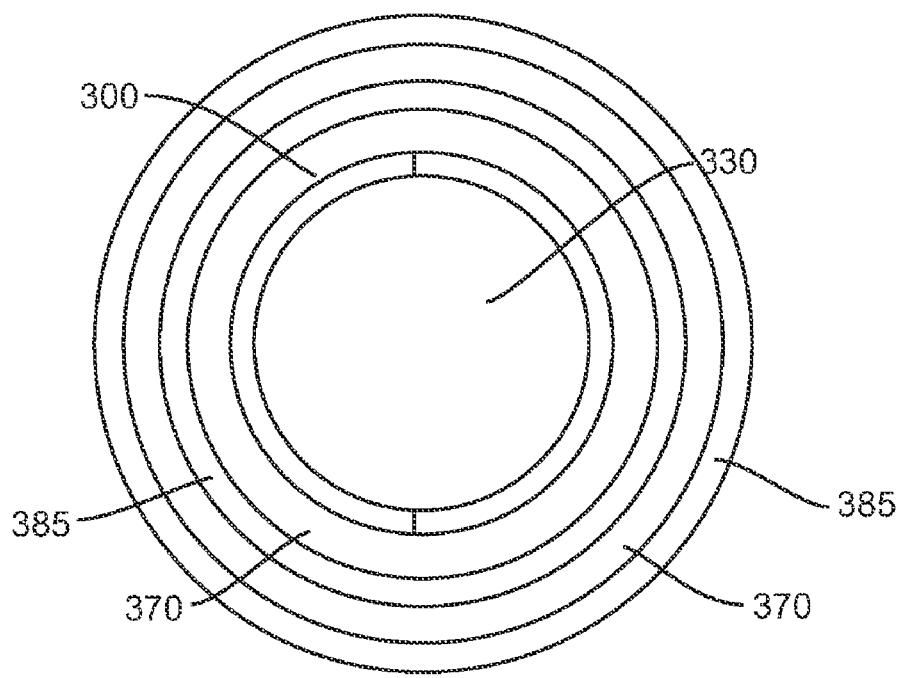
FIG. 7b is a top end view of the needle with two dilator tubes positioned over the needle in accordance with the principles of the present disclosure.
Figure 8:
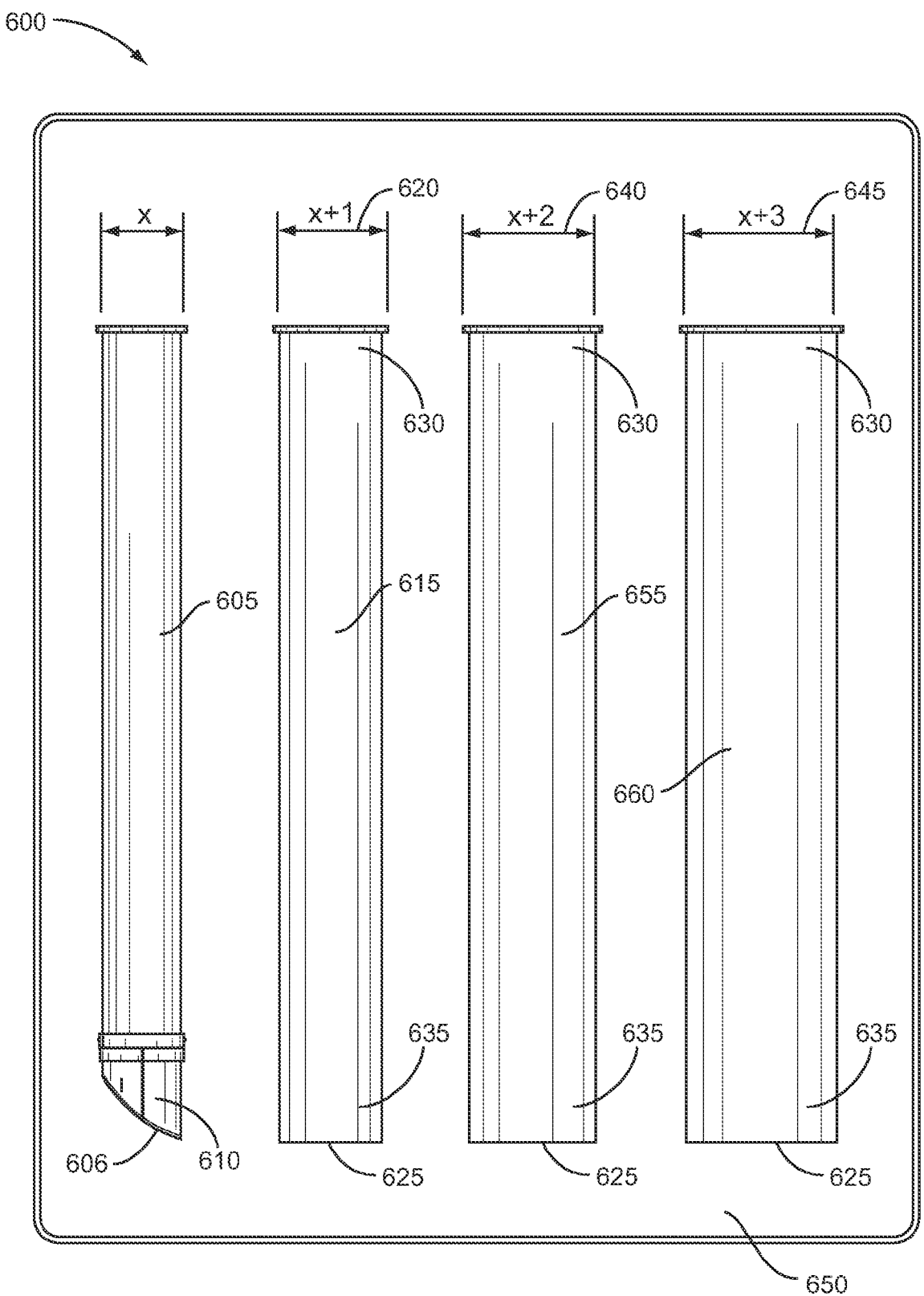
FIG. 8 shows cut-away side views of the needle assembly kit with several dilator tubes in accordance with the principles of the present disclosure.

Still yet another embodiment of the present invention is shown in FIGS. 6-8. In this embodiment, needle assembly 300 comprises a needle 305 and a needle head 310 attached to the needle 305 at the distal end 335. The needle 305 has a particular diameter 345 and an opening 320 at the proximal end 325 of needle 305. The needle head 310 having a cutting edge 315 can be expandable as described above or a solid non-expandable head. The needle head 310 is attached to the needle at attachment point 340. As with the embodiments in FIGS. 1-5, the needle head 310 and the needle 305 can be attached by friction fit, screw and thread, tongue and groove, protuberance and/or hole arrangements.

Also part of the needle assembly 300 of the present invention is a dilator tube 385 that has a diameter 350 that is larger than the diameter 345 of the needle 305. The dilator tube 385 has an opening 360 at the proximal end 365 and a blunt non-cutting edge 380 at the distal end 375. The dilator tube 385 is configured to slide over the outside of the needle 305 to the access hole cut in the patient. Once at the access hole, the dilator tube can be gently advanced in between the needle and the outer perimeter of the access hole to stretch the access hole to a larger diameter without further cutting into the patient. For example, using the needle assembly 300 in connection with intervertebral disc therapies, the cutting edge can be thrusted into the annulus of a disc and the dilator tube used to stretch the annulus to a larger diameter without further cutting the access hole. In this manner, the initial needle hole remains small which minimizes tissue damage but then expands the access hole so that it can be used to facilitate therapy delivery or tissue/fluid evacuation requiring a larger needle.

FIG. 7a shows a cross sectional view of the needle 305 and a dilator tube 385 over the outside of the needle. The lumen 330 of needle 305 is smaller than the lumen of the dilator tube 370. Similarly, FIG. 7b shows a configuration of the present invention having two dilator tubes. Here, the first dilator tube 385 has a larger diameter than the needle 305 but a smaller diameter than the second dilator tube 395. In this embodiment of the present invention, the first dilator tube 385 can be placed over needle 305 and the second dilator tube 395 can be placed over the first dilator tube 385 to produce a diameter even larger than the first dilator tube 385. Additional configurations of the present invention can have a plurality of dilator tubes, each having increasing diameters. The number of dilator tubes that can be used is a function of the procedure/therapy the needle assembly is being used for, the type of tissue in which the needle is being used on and the condition of the patient.

FIG. 8 is directed to a kit having a needle 605 having a needle head 610 with a cutting edge 606. The needle having a particular diameter. Also included in the kit are three dilator tubes 615, 655, and 660 each having a distal end 635 and a proximal end 630. The distal ends 635 having a blunt end 625. Each of the dilator tubes having increasing diameters so that they can fit one over the other. That is, dilator tube 615 has a diameter 620 that is larger than the diameter of needle 605. Dilator tube 655 having a diameter 640 that is larger than the diameter 620 of dilator tube 615 but smaller than the diameter 645 of dilator tube 660 so that dilator tube 660 can be placed over dilator tube 630 to enlarge the diameter of the original access hole even larger without further cutting into the tissue. As stated above, although three dilator tubes are shown, the number and size of the dilator tubes in a kit can vary from one to about 10.

The dilator tubes can be coated with a biological compatible lubricate and/or coating designed to reduce tissue damage as the dilators are advanced into the small access hole cut by the cutting edge. In addition, the cutting edge can also be coated to reduce excess bleeding and or trauma to the tissue being cut. The kit can be a one time use disposable kit or in the alternative the needle and the dilators can be made from durable material such as, stainless steel, ceramics, composites and the like, that can be sterilized between uses. The dilator tubes and the needles can be stamped with indicia that identify the diameter of the dilator tube and/or sequence of the tube to be used.

It is envisioned that the components of the needle assembly embodiments of the present invention described herein can be manufactured via various methods. For example, the components of the needle assembly system can be manufactured and assembled via injection-molding, insert-molding, overmolding, compression molding, transfer molding, co-extrusion, pultrusion, dip-coating, spray-coating, powder-coating, porous-coating, milling from a solid stock material, and their combinations. One skilled in the art, however, will realize that such materials and fabrication methods suitable for assembly and manufacture, in accordance with the present disclosure, would be appropriate.

The present invention is also directed to methods using the needle assemblies of the present invention. The different methods used depend on the needle assembly used and the procedure being conducted. One method of the present invention is a method of facilitating delivery of a therapeutic agent and/or evacuating tissue/fluid to/from an intervertebral disc. This method uses one of the needle assemblies having and expandable head discussed above. Providing the needle assembly discussed above having an expandable head. Once in position the needle the cutting edge of the expandable needle head is gently thrusted into a surface of an intervertebral disc to facilitate cutting into said intervertebral disc. Once in, the expandable needle head of the needle is expanded and delivery and/or evacuation of tissue/fluid through the expandable needle head into the hollow shaft of the needle can be achieved. Upon completion of the therapeutic task, the expandable needle head of the needle is compressed and the needle is removed from the intervertebral disc.

A second method using the dilator tube disclosed above is provided and has the following steps. The method is for facilitating delivery of a therapeutic agent and/or evacuating tissue/fluid to/from an intervertebral disc or other part of a patient and once in position, the orthopedic needle assembly is gently advanced so that the cutting edge cuts into the annulus of the intervertebral vertebral disc. Once the needle is cut into the intervertebral disc, at least one dilator tube is positioned over the needle and advanced gently down the length of the needle into the annulus of the intervertebral disc to produce an expanded opening. This step can be repeated should multiple dilators be required. Once the proper number of dilator tubes are in place the therapeutic procedure such as delivering and/or evacuating tissue/fluid through the expanded opening. Once the therapeutic procedure is completed, the dilator tubes and eventually the needle can be removed from the annulus of the intervertebral disc of the patient.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An orthopedic needle assembly comprising:
a needle comprising a hollow shaft having opposed distal and proximal ends and a lumen extending from said distal end of said hollow shaft and terminating at an opening on said proximal end of said hollow shaft, said distal end having an expandable needle head having 2 to 6 segments and a cutting surface,
   said segments configured to be interconnected to each other by a plurality of ductile hinges in an alternating arrangement to form a substantially cylindrical tube, said substantially cylindrical tube configured to expand or compress from a first diameter to a second diameter by deformation of said ductile hinges without substantial deformation of said segments, said plurality of ductile hinges configured to deform resiliently upon radial expansion or compression of said expandable needle head;
   said cutting surface configured for penetration into an intervertebral disc of a patient wherein said cutting surface comprises a sharpened edge extending along a portion of a bottom of said expandable needle head; and
   a movable band positioned around a portion of said expandable needle head and said segments and ductile hinges of said expandable needle head, wherein the expandable needle head is configured to expand to an expanded diameter upon movement of said movable band from a first position to a second position and said segments and ductile hinges of said expandable needle head are configured to compress to a diameter smaller than said expanded diameter upon movement of said movable band from said second position back to said first position.

2. The orthopedic needle assembly of claim 1 wherein said Gutting sharpened edge of said needle is about 12 gauge to about 16 gauge.

3. The orthopedic needle assembly of claim 1, wherein said plurality of ductile hinges have different widths depending on their location in said expandable needle head.

4. The orthopedic needle assembly of claim 1 further comprising a manipulator handle having a trigger configured to cause movement of said movable band from said first position to said second position thereby causing said segments and ductile hinges of said expandable needle head to expand to an expanded diameter upon actuating said trigger axially from a first position to a second position and to cause compression of said segments and ductile hinges of said expandable needle head to a diameter smaller than said expanded diameter of said expandable needle head upon actuating said trigger axially back to said first position.

5. An orthopedic needle assembly kit comprising:
a needle comprising a hollow shaft having opposed distal and proximal ends and a lumen extending from said distal end of said hollow shaft and terminating at an opening on said proximal end of said hollow shaft, said distal end configured to accept an expandable needle head;
a multiple of expandable needle heads each configured to removably attach to said distal end of said hollow shaft, each of said expandable needle heads having 2 to 6 segments and a cutting surface, said segments configured to be interconnected to each other by a plurality of ductile hinges in an alternating arrangement to form a substantially cylindrical tube, said substantially cylindrical tube configured to expand or compress from a first diameter to a second diameter by deformation of said ductile hinges without substantial deformation of said segments, said plurality of ductile hinges configured to deform resiliently upon radial expansion or compression of said expandable needle head;
said cutting surface configured for penetration into an intervertebral disc of a patient wherein said cutting surface comprises a sharpened edge extending along a portion of a bottom of each of said expandable needle heads and each of said expandable heads having an increasing number of expandable segments; and
a movable band positioned around a portion of said expandable needle head and said segments and ductile hinges of said expandable needle head configured to expand to an expanded diameter upon movement of said movable band from a first position to a second position and said segments and ductile hinges of said expandable needle head configured to compress to a diameter smaller than said expanded diameter upon movement of said movable band from said second position back to said first position.

6. The orthopedic needle assembly kit of claim 5 comprising a first, second, third, fourth and fifth expandable needle head, said first expandable needle head configured to have 2 expandable segments, said second expandable needle head configured to have 3 expandable segments, said third expandable needle head configured to have 4 expandable segments, said fourth expandable needle head configured to have 5 expandable segments, and said sixth 6 expandable needle head configured to have 6 expandable segments.

7. The orthopedic needle assembly kit of claim 6 wherein each of said expandable needle heads are configured to have indicia indicating the number of segments, orientation indicator and the diameter of said expandable needle head when expanded.

8. The orthopedic needle assembly kit of claim 7 further comprising a manipulator handle configured to removably attach to each of said expandable needle heads, said trigger configured to cause movement of a movable band positioned around said expandable needle heads from a first position to a second position thereby causing said segments and ductile hinges of said expandable needle head to expand to an expanded diameter upon actuating said trigger axially from a first position to as second position and said trigger configured to cause said movement of said band back to said first position to cause compression of said segments and ductile hinges of said expandable needle head to a diameter smaller than said expanded diameter of said expandable needle head upon actuating said trigger axially back to said first position.

9. A method of facilitating delivery of a therapeutic agent and/or evacuating tissue/fluid to/from an intervertebral disc comprising;
  (a) providing an orthopedic needle assembly comprising: a needle comprising a hollow shaft having opposed distal and proximal ends and a lumen extending from said distal end of said hollow shaft and terminating at an opening on said proximal end of said hollow shaft, said distal end having an expandable needle head having 2 to 6 segments and a cutting surface, said segments configured to be interconnected to each other by a plurality of ductile hinges in an alternating arrangement to form a substantially cylindrical tube, said substantially cylindrical tube configured to expand or compress from a first diameter to a second diameter by deformation of said ductile hinges without substantial deformation of said segments, said plurality of ductile hinges configured to deform resiliently upon radial expansion or compression of said expandable needle head;
  said cutting surface configured for penetration into an intervertebral disc of a patient wherein said cutting surface comprises a sharpened edge extending along a portion of a bottom of said expandable needle head; and
  a movable band positioned around a portion of said expandable needle head and said segments and ductile hinges of said expandable needle head, wherein the expandable needle head is configured to expand to an expanded diameter upon movement of said movable band from a first position to a second position and said segments and ductile hinges of said expandable needle head are configured to compress to a diameter smaller than said expanded diameter upon movement of said movable band from said second position back to said first position;
  (b) thrusting said sharpened edge into a surface of an intervertebral disc to facilitate cutting into said intervertebral disc;
  (c) expanding said expandable needle head inside said intervertebral disc;
  (d) delivering or evacuating tissue/fluid through said expandable needle head into said hollow shaft; and
  (e) compressing said expandable needle head and removing said expandable needle head from said intervertebral disc.

* * * * *

UNITED STATES PATENT AND TRADEMARK OFFICE
CERTIFICATE OF CORRECTION

PATENT NO.       : 7,879,009 B1                                   Page 1 of 1
APPLICATION NO.  : 12/696153
DATED            : February 1, 2011
INVENTOR(S)      : Haddock et al.

It is certified that error appears in the above-identified patent and that said Letters Patent is hereby corrected as shown below:

On the Title Pg, Item (73), under "Assignee", Line 1, delete "Inc.," and insert
-- Inc., Warsaw, IN(US) --, therefor.

In Column 10, Line 9, in Claim 2, delete "Gutting sharpened" and insert -- sharpened --, therefor.

In Column 11, Line 1, in Claim 6, delete "sixth 6" and insert -- fifth --, therefor.

In Column 11, Line 24, in Claim 9, delete "comprising;" and insert -- comprising: --, therefor.

Signed and Sealed this
Twelfth Day of April, 2011

David J. Kappos
*Director of the United States Patent and Trademark Office*